(12) United States Patent
Limmert et al.

(10) Patent No.: US 8,920,944 B2
(45) Date of Patent: Dec. 30, 2014

(54) USE OF A PRECURSOR OF AN N-DOPANT FOR DOPING AN ORGANIC SEMICONDUCTIVE MATERIAL, PRECURSOR AND ELECTRONIC OR OPTOELECTRONIC COMPONENT

(75) Inventors: Michael Limmert, Dresden (DE); Andrea Lux, Dresden (DE); Horst Hartmann, Dresden (DE)

(73) Assignee: Novaled AG, Dresden (DE)

( * ) Notice: Subject to any disclaimer, the term of this patent is extended or adjusted under 35 U.S.C. 154(b) by 1285 days.

(21) Appl. No.: 12/665,887

(22) PCT Filed: Jun. 20, 2008

(86) PCT No.: PCT/DE2008/000995
§ 371 (c)(1),
(2), (4) Date: Mar. 15, 2010

(87) PCT Pub. No.: WO2009/000237
PCT Pub. Date: Dec. 31, 2008

(65) Prior Publication Data
US 2010/0187515 A1    Jul. 29, 2010

(30) Foreign Application Priority Data
Jun. 22, 2007    (EP) ..................................... 07012228

(51) Int. Cl.
| | | |
|---|---|---|
| H01L 51/30 | (2006.01) | |
| H01L 51/54 | (2006.01) | |
| H01L 51/46 | (2006.01) | |
| C07D 487/12 | (2006.01) | |
| C07F 7/02 | (2006.01) | |
| C07D 498/04 | (2006.01) | |
| H01L 51/00 | (2006.01) | |
| C07D 487/16 | (2006.01) | |
| H01L 51/50 | (2006.01) | |

(52) U.S. Cl.
CPC ............. *C07D 487/16* (2013.01); *Y02E 10/549* (2013.01); *H01L 51/0059* (2013.01); *H01L 51/002* (2013.01); *H01L 51/0072* (2013.01); *H01L 51/5088* (2013.01); *H01L 51/5012* (2013.01); *H01L 51/0094* (2013.01); *H01L 51/5096* (2013.01); *H01L 51/5052* (2013.01); *H01L 51/0052* (2013.01); *Y10S 428/917* (2013.01)
USPC ......... 428/690; 428/917; 428/411.1; 428/336; 544/247; 544/229; 544/245; 544/250

(58) Field of Classification Search
None
See application file for complete search history.

(56) References Cited

U.S. PATENT DOCUMENTS 8,134,146 B2 *   3/2012   Limmert et al. ................ 257/40
2007/0252140 A1 *  11/2007   Limmert et al. ................ 257/40

OTHER PUBLICATIONS

Baradarani et al., "A Naphthalene-Fused Tricyclic Orthoamide," Acta Crystallographica Section C, 1995, 51 (7):1345-1347.

(Continued)

*Primary Examiner* — J. L. Yang
(74) *Attorney, Agent, or Firm* — Sutherland Asbill & Brennan LLP

(57) ABSTRACT

Use of a precursor of an n-dopant for doping an organic semiconductive material, as a blocking layer, as a charge injection layer, as an electrode material, as a storage material or as a semiconductor material itself in electronic or optoelectronic components, the precursor being selected from the following formulae 1-3c:

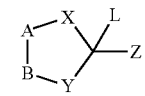

1

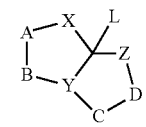

2

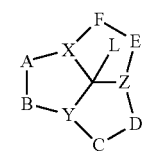

3

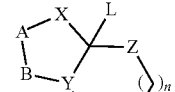

2a

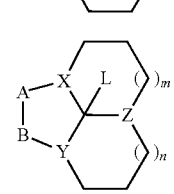

3a

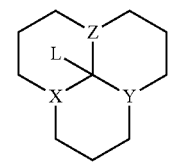

3b

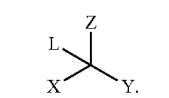

3c

13 Claims, No Drawings

(56) References Cited

OTHER PUBLICATIONS

Vaid et al., "Investigations of the 9,10-Diphenylacridyl Radical as an Isostructural Dopant for the Molecular Semiconductor 9,10-Diphenylanthracene," Chem. Mater, 2003, 15:4292-4299.

Werner et al., "Pyronin B as a Donor for n-type Doping of Organic Thin Films," Applied Physics Letters, 2003, 83:4495-4497.

Translation of Japanese Office Action mailed Aug. 6, 2013 for Japanese Application No. 2010-512510 (3 pages).

Alder, Roger, W., New Synthetic Routes to Macrocyclic Triamines, J. Chem. Soc., Chem. Commun., 1992, pp. 507-508.

Bazinet, Patrick, Design of Sterically Lamanding, Electron-Rich Carbene Ligands with the Perimidine Scaffold, Organometallics 2007, 26, pp. 2885-2895.

Brook, A. G., The Formation of Tetraarylsilanes from the Reactions of Triaylsilylmetallic Compounds. II. Reactions with Triarylsilanes, A. G. Book and Henry Gilman, vol. 76, May 5, 1954, pp. 2333-2338.

Bssaibis, Mohamed, Preparation of Dithiadiazafulvalene Precursors: 2-Piperidino-2,3-dihydro-1,3-thiazoles or 2-Unsubstituted 2,3-Dihydro-1,3-thiazoles from the Reduction of the Corresponding 2-Piperidino Mesoionic Thiazoles, J. Chem. Soc. Perkin Trans. 1 1994, pp. 1469-1472.

Cheeseman, G. W. H., Quinoxalines and Related Compounds. Part II. The Prepration of NN"-Dimethyl-o-phenylenediamine and N.-Methyl-o-phenylenediamine, Part I, J., 1955, 1804, pp. 3308-3310.

Csihony, Szilard, Single-Component Catalyst/Initiators for the Organocatalytic Ring-Opening Polymerization of Lactide, J. Am. Chem. Soc. 2005, 127, pp. 9079-9084.

Eid, Samar, Trithiaazafulvalene: A Promising Building Block between Tetrathiafulalene, American Chemical Society, 2006, pp. 2377-2380.

Furstner, Alois, Comparative Investigation of Ruthenium-Based Metathesis Catalysts Bearing N-Heterocyclic Carbene (NHC) Ligands, Chem. Eur, J. 2001, pp. 3236-3253, 7, No. 15.

Kantleher, Willi, Beitrage zur Synthese von Orthocarbonsaureamiden, J. Prakt. Chem., 2002, pp. 256-268, 342, No. 3.

Kantlehner, W., Products Subclass 6: Othro Amides (Alkane-1,1,1-trimines), Science of Synthesis, pp. 795-841, 2006.

Khalaf, Abedawn, Unexpected Dealkylation During Nucleophilic Substitution: Sysnthesis of 2-N,N-Dialkylaminon Benzoxazoles and Benzothiazoles, Elsevier Science Ltd. 2000, pp. 8567-8571.

Kohn, Randolf, Syntheses and Structures of 13-Substituted 1,5,9-Trazatricolyclo[7.3.1.0 5,13]-tridecanes and Their Copper(II) Cloride Complexes, Chem. Ber. 1996, pp. 21-24, 129.

Kulkarni, Abhishek P., Electron Transport Metarials for Organic Light-Emitting Diodes, American Chemical Society, 2004, pp. 4556-4573.

Ludvk, J., Electrochemical Generation of Triplet States Simplified Estimation of Triplet Energies by Electrogenerate Chemiluminescence Based on the Anodic Cleavage of Dimetric Dhydroheteroarenes, J. Electroana. Chem., 1984, pp. 141-156.

Hasegawa, Eietsu, Contrastive Phtoreduction Pathways of Benzophenones Governed by Regiospecific Deprotonation of Imidazoline Radical Cations and Additive Effects, J. Org. Chem., 2005, pp. 9632-9635.

Korotkikh, N. I., Reaction of 1,3-dibenzyl-2-cynomethyl-2H-benzimidazoline, SciFinder Scholar, May 17, 2010, pp. 32-38.

Malik, Abdul, Some Extensions of von Brun (BrCN) Recation on Organic Bases: Part II, pp. 512-518, 1982.

Ried, Von Walter, Rignschlubreaktionen mit 2-Amino-benzo-bzw, naphtho-imidazolen, Journal fur praktische Chemi, 1959, pp. 132-149.

Wawer, Iwona, 1 H and 13 C Nuclear Magnetic Resonance Identification of the Products of the Reaction of NN-Dialkylformamide Dimethyl Acetails with Secondary Amines, J. Chem. Soc. Perkin Tans. 1985, pp. 1669-1671.

Yokoi, Hajime, Photochemical Doping of TCNQ by Photoinduced Electron Transfer and C-C Cleavage of Radical Cation, The Chemical Society of Japan, 1999, pp. 241-242.

* cited by examiner

USE OF A PRECURSOR OF AN N-DOPANT FOR DOPING AN ORGANIC SEMICONDUCTIVE MATERIAL, PRECURSOR AND ELECTRONIC OR OPTOELECTRONIC COMPONENT

CROSS-REFERENCE TO RELATED APPLICATION

This is a submission pursuant to 35 U.S.C. 154(d)(4) to enter the national stage under 35 U.S.C. 371 for PCT/DE2008/000995 filed Jun. 20, 2008. Priority is claimed under 35 U.S.C. 119(a) and 35 U.S.C. 365(h) to European Patent Application Number 07012228.8 filed Jun. 22, 2007. The subject matters of PCT/DE2008/000995 and European Patent Application Number 07012228.8 are hereby expressly incorporated herein by reference in their entirety.

The present invention relates to the use of a precursor of an n-dopant for doping an organic semiconductive material, as a blocking layer, as a charge injection layer, as an electrode material, as a storage material or as a semiconductor layer itself in electronic or optoelectronic components, to the corresponding precursor, organic semiconductive material and also electronic or optoelectronic components.

It is known, to use doping to modify organic semiconductors with regard to their electrical properties, in particular their electrical conductivity, as is the case also in respect of inorganic semiconductors, such as silicon semiconductors. Here, an increase in the conductivity, which is initially very low, and also, depending on the type of dopant used, a change in the Fermi level of the semiconductor is achieved by generating charge carriers in the matrix material. In this case, doping leads to an increase in the conductivity of charge transport layers, as a result of which ohmic losses are reduced, and to an improved transfer of the charge carriers between the contacts and the organic layer. Doping in the conductivity sense is characterized by a charge transfer from the dopant to a nearby matrix molecule (n-doping, electron conductivity increased) or by the transfer of an electron from a matrix molecule to a nearby dopant (p-doping, hole conductivity increased). The charge transfer may take place to an incomplete or complete extent and can be determined for example by interpreting vibration bands of an FTIR measurement (Fourier-transformed infrared spectroscopy).

The inorganic dopants used to date, such as alkali or alkaline earth metals (e.g. cesium) or Lewis acids (e.g. $FeCl_3$), are usually disadvantageous in the case of organic matrix materials on account of their high diffusion coefficient, since the function and stability of the electronic components is impaired. These inorganic dopants are also associated with difficulties in production, since they usually have a high vapor pressure at room temperature and may contaminate the production systems in vacuum processes. Alkali and alkaline earth metals in particular have the further disadvantage that use thereof is made more difficult on account of their high reactivity with air. These known disadvantages are said to be avoided by using molecular n-dopants.

Strong molecular dopants may be dopants which act directly (i.e. those which, like alkali metals, develop their effect directly and without any further activating measures; see above). Examples of these are tetrathiafulvalenes or decamethylcobaltocene (WO 03/088271 A). However, one significant disadvantage of these substances is a pronounced sensitivity to atmospheric substances (oxygen and water), so that usually special measures have to be taken when they are used (e.g. inert gas atmosphere).

One alternative to this consists in using a suitable precursor compound which releases the active species when suitably activated, for example by excitation with light. Examples of these include dimers of the diphenylmethyl radical (H. Yokoi et al., Chem. Lett. 1999, 241-242) or else Leuco Crystal Violet (DE 10307125 A1). In this case, however, the actual doping effect is relatively small; in particular, only identified acceptors can be doped with diphenylmethyl radicals. One particularly effective type of dimers are bipyridinyls and in particular biimidazolyls (J. Ludvik, F. Pragst et al., J. Elelctroanal. Chem. Interfac. Electrochem. 1984, 180(1-2), 141-156). However, in this case there is the difficulty of obtaining these synthetically, which for these materials requires electrochemical expertise. This particular technique is in turn a significant limiting factor for technical production since electrolysis methods, apart from prominent exceptions such as fused salt electrolysis, are barely used in the case of fine chemicals.

The fact that imidazolines, more specifically 2H-imidazolines, may in principle be capable of being doped is described in E. Hasegawa et al. J. Org. Chem. 2005, 70, 9632-9635. Here, an electron transfer after optical excitation is postulated as the first step in a complex reaction sequence. However, this also means that, for an n-dopant, a structure has to be found which as far as possible suppresses these successive reactions and thus sustainably maintains the doping effect.

The object of the present invention is to overcome the disadvantages of the prior art and to provide a possibility for obtaining an n-doping of an organic semiconductive material in a simple and effective manner, the n-dopant obtained having a high donicity (effective doping strength) and also being easily modifiable. In addition, novel compounds are to be provided which are suitable as a corresponding precursor of an n-dopant. Furthermore, organic semiconductive materials and also electronic and optoelectronic components are to be provided.

The first object is achieved by the use of a precursor of an n-dopant according to claim 1. Further objects are achieved by independent claims 9, 10 and 12. Preferred embodiments emerge from the dependent claims.

It has surprisingly been found that the disadvantages of the prior art can be overcome if the precursor of an n-dopant is used for doping an organic semiconductive material and for the other purposes as specified in claim 1. In these precursors, a labile bond is irreversibly cleaved by means of suitable (usually optical) excitation. In the compounds used according to the invention, upon excitation, the substituent L is discharged as a neutral radical (leaving group). The actual dopant, the intermediate radical, is released as a result, which on account of its $7\pi$ electron structure is a very effective reducing agent; the aim is to discharge its surplus electron in order to form a highly stable, aromatic cation. The recipient of the electron is preferably a weak acceptor (for example the surrounding host material, hereinafter referred to as the matrix). This means that the acceptor is reduced, i.e. electrically doped, to form the radical anion.

In the use according to the invention, at least the following components can be generated as end stages of a successful doping operation: a highly stable cation, a formally redox-inactive radical and a radical anion of the surrounding matrix. In this case, the redox-inactive radical may either remain as such, may optionally dimerize in solution to form an intermolecular subsequent product with closed electron shells, or it may also in particular cases (1,2-diradical) become intramolecularly saturated to form an alkene.

In principle, the doping may take place via several alternative reaction paths, which may depend on electronic and steric conditions of the materials used:

Homolysis after (preferably) optical excitation into two radicals (as described above). Cleavage into a neutral radical, with the aim of discharging its electron to the surroundings, and into a redox-inert, stable radical.

Electron transfer from the complete precursor by (preferably) optical excitation and subsequent decomposition of the intermediate radical cation into a cation and into a redox-inert, stable radical.

Heterolysis alter (preferably) optical excitation into a cation and an anion; here, the aim is for the latter to convert via electron discharge into a redox-inert, stable radical. This cleavage may take place in the case of hydridic variants (i.e. L=H).

The effectiveness of the electron transfer, i.e. the dopant strength, depends essentially on three parameters:

Reduction potential of the cation (preferably <−2.3 V vs. ferrocene/ferrocene', particularly preferably <−2.6 V, most preferably <−2.8 V).

Tendency of the leaving group to form a radical. For example, this tendency is very low in the case of aryl groups, so that cleavage is rather improbable in the ease of $R=C_6H_5$. Conversely, benzyl (i.e. $R=CH_2C_6H_5$) is an effectively stabilized radical, so that there is in this case a high tendency towards cleavage.

Strength of the C-L bond. This depends on steric and electronic conditions.

Compared to the prior art, the concept according to the invention oilers a number of advantages which will be explained below: good synthetic access; easy to modify; high dopant strength; broad field of application.

Furthermore, the precursors have a high stability with respect to oxygen and moisture (in particular compared to dopants such as decamethylcobaltocene), so that no special protective measures (inert gas atmosphere) have to be taken when they are used.

Syntheses of Selected Chemical Compounds

The compounds are accessible via various synthesis routes.

The literature includes the reaction of suitable 1,2-diaminobenzoles with aldehydes or ketones, the corresponding imidazolines being formed by condensation of water (G. W. H. Cheeseman, J. Chem. Soc. 1955, 3308-3310).

According to the invention, however, it is more advantageous to react an imidazolium ion with a suitable anion as a strong nucleophile, which results in the dopant as neutral compound. Compared to the prior art, this route has the advantages of a shorter synthesis sequence and much milder reaction conditions.

Preferred Synthesis Method:

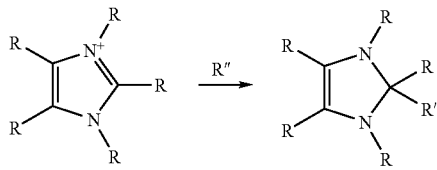

General Procedure: 2-aminobenzimidazoles
2-aminobenzimidazole Derivates

The synthesis of 2-aminobenzimidazole derivates from suitable aromatic diamines takes place as described in the literature (W. Ried et al., J. Prakt. Chem. 1959, 8, 132-149).

Imidazolium Ions
General Procedure: Polycyclic Guanidinium Salts

Bridging to guanidinium derivatives takes place in the same way for all derivatives: 10 mmol (2.0 g) of 1,3-dibromopropane and 15 mmol (1.9 g) of $K_2CO_3$ in DMF are added to 5 mmol of the corresponding 2-aminobenzimidazole. The mixture is heated with stirring for 5 h at 60° C., then for 6 h at 90° C. and finally for a further 6 h at 135° C. The insoluble fraction is filtered off and the filtrate is concentrated. The product precipitates as a bromide salt, which is dried in vacuo.

Silyl Anions
General Procedure: Alkali Metal Triorganyl Silyls as Reaction Components The synthesis takes place as described in the literature (A. G. Brook et al., J. Am. Chem. Soc. 1954, 76, 2333-2338).

Further organometallics are either commercially available (as an organolithium or organomagnesium compound) or are obtained in situ using standard methods (e.g. deprotonation with butyllithium in diethyl ether)

Dopant Syntheses

A: General Procedure for Dopants where L=H

The synthesis takes place as described in the literature (R. W. Alder et al., J. Chem. Soc. Chem. Commun. 1992, 507-508)

B: General Procedure: 2,2-dialkylimidazolines or Ortho-carboxylic Acid Amides and Derivatives The corresponding cation, for example a guanidinium salt, is suspended in THF, and an organometallic coupling partner is added with stirring at RT. The conversion is demonstrated by the fact that the insoluble salt dissolves and finally a milky solution is obtained. Water is added to this solution and extraction takes place with diethyl ether. The ether phase is dried over magnesium sulfate, filtered and concentrated. The product is obtained as a colorless solid.

Compound 11
Synthesis According to Procedure B

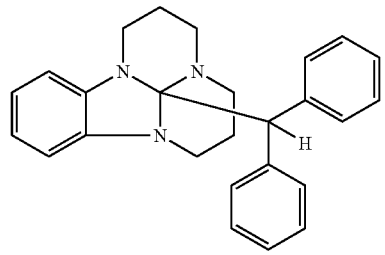 [SMILES: c1ccc(C(c2ccccc2)C23N4CCCN2c2ccccc2N3CCC4)cc1]

$^1$H-NMR (500 MHz, THF-$d_8$): δ=7.47, m, 4H; 7.05-7.25, m, 6H; 6.34, m, 2H; 6.23, m, 2H; 5.31, s, 1H; 3.24, m, 4H; 2.92, m, 2H; 2.54, m, 2H; 1.84, m, 2H; 1.21, m, 2H.

Compound 12
Synthesis According to Procedure B

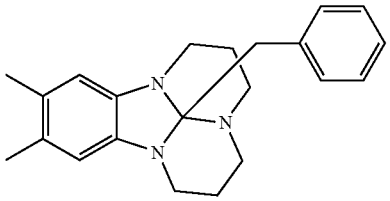 [SMILES: Cc1cc2c(cc1C)N1CCCN3CCCN2C31Cc1ccccc1]

$^1$H-NMR (500 MHz, THF-$d_8$): δ=7.26, m, 2H; 7.10, m, 2H; 7.05, m, 1H; 6.06, s, 2H; 3.52, m, 2H; 3.46, s, 2H; 3.36, m, 2H; 2.98, m, 2H; 2.46, m, 2H; 2.04, s, 6H; 1.95, m, 2H; 1.32, m, 2H.

Compound 13

Synthesis According to Procedure B

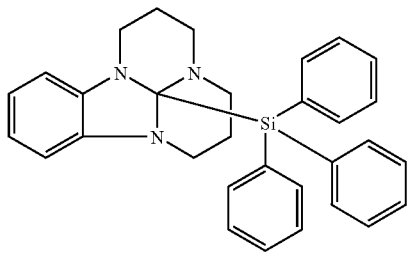 [SMILES: c1ccc([Si](c2ccccc2)(c2ccccc2)C23N4CCCN2c2ccccc2N3CCC4)cc1]

$^1$H-NMR (500 MHz, THF-d$_8$): δ=7.78, m, 6H; 7.35, m, 3H; 7.28, m, 6H; 6.51, m, 2H; 6.34, m, 2H; 3.34, m, 2H; 3.04, m, 2H, 2.83, m, 4H; 1.83, m, 2H; 1.17, m, 2H.

Compound 14

Synthesis According to Procedure A

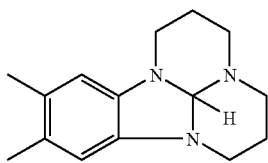

$^1$H-NMR (500 MHz, CDCl$_3$): δ=6.15, s, 2H; 4.47, s, 1H; 3.66, m, 2H; 3.15, m, 2H; 2.54, m, 2H; 2.25, m, 2H; 2.16, s, 6H; 1.80, m, 2H; 1.30, m, 2H.

Compound 15

Synthesis According to Procedure A

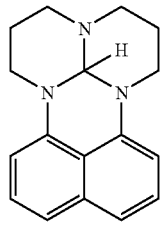

$^1$H-NMR (500 MHz, CDCl$_3$): δ=7.22, m, 2H; 7.09, m, 2H; 6.56, m, 2H; 4.58, s, 1H; 4.17, m, 2H; 3.05, m, 2H; 2.93, m, 2H; 2.38, m, 2H, 2.25, m, 2H; 1.39, m, 2H.

Compound 16

Synthesis According to Procedure A

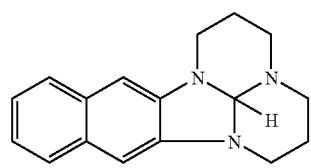

$^1$H-NMR (500 MHz, CDCl$_3$): δ=7.52, m, 2H; 7.15, m, 2H; 6.65, s, 2H; 4.63, s, 1H; 3.87, m, 2H; 3.29, m, 2H; 2.69, m, 2H, 2.36, m, 2H; 1.97, m, 2H; 1.47, m, 2H.

Compound 17 (According to Type 3b)

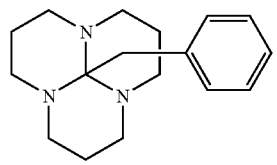 [SMILES: c1ccc(CC23N4CCCN2CCCN3CCC4)cc1]

The starting compound (tricyclic guanidinium cation) was synthesized using a procedure described in the literature (R. W. Alder et al, *J. Chem. Soc. Chem. Commun.* 1992, 507). The conversion to the desired product can be done according to standard procedure B. Alternatively, the compound according to type 3b can be produced according: R. D. Köhn, G. Seifert et al, *Chem. Ber,* 1996, 129(19), 21-24.

$^1$H-NMR (500 MHz, DMOS-d$_6$): δ=7.43, d, 2H; 7.14, t, 2H; 7.06, t, 1H; 3.25, s, 2H; 2.7-2.85, m, 12H; 1.87, m, 3H; 1.21, m, 3H.

Compound 18 (According to Type 2a)

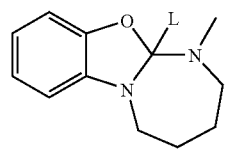

L=H

The starting compound (bicyclic 2-amino-benzoxazole) was synthesized using a procedure described in the literature (A. I. Khalaf et al., *Tetrahedron* 2000, 56, 8567). The conversion to the desired product takes place as standard according to procedure A.

$^1$H-NMR (500 MHz, DMSO-d$_6$): δ=6.55, m, 1H; 6.38, m 2H; 6.29, m, 1H; 4.45, s, 1H; 2.94, t, 2H; 2.12, t, 2H; 2.09, s, 3H; 1.51-1.38, m, 4H.

Compound 19 (According to Type 2a)

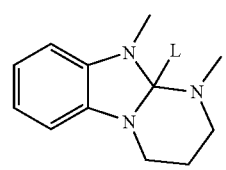

L=H

The starting compound was first synthesized according to WO 2005/086251 A2 up to the intermediate of 2,3,4,10-tetrahydropyrimido[1,2-a]benzimidazol, which was then alkylated in DMF with heating to reflux in the presence of methyl iodide to form the imidazolium ion.

The subsequent conversion to the desired product takes place as standard according to procedure A.

$^1$H-NMR (500 MHz, DMSO-d$_6$): δ=6.55, m, 2H; 6.41, m, 2H; 4.64, s, 1H; 3.10, s, 3H; 3.03, t, 2H; 2.41, t, 2H; 2.21, s, 3H; 1.745, m, 2H.

Compounds According to Type I

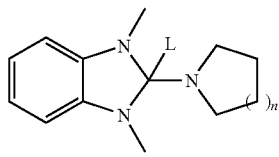

Compounds according to this type with L=H and X, Y, Z=N are for example disclosed in N. I. Korotkikh, O. V: Knishevitskii et al., *Ukr. Khim. Zhur.* 2006, 72(7-8), 32-38. W. Kanthlener, *Science of Synthesis* 2005, 22, 795-841.

Variants:

Compounds according to the general type I with L=H; X, Y=NR and Z=OR are for example disclosed in S. Csihony, D. Culkin et al., *J. Am. Chem. Soc.* 2005, 127(251), 9079-9084. P. Bazinet, T.-G. Ong, et al., *Organometallics* 2007, 26(11), 2885-2895. A. Fürstner, L. Ackermann, et al., *Chem. Eur. J.* 2001, 7(15), 3236-3253.

Compounds according to general type I with L=H; X=NR, Y=O and Z=$NR_2$ are for example disclosed in A. Malik, N. Afza, S. Siddiqui, *Z. Naturforsch. B* 1982, 37B(4), 512-18.

Compounds according to the general type I with L=H; X=S, NR, Y=S and Z=$NR_2$ are for example disclosed in S. Eid. M. Guerro, et al., *Org. Lett.* 2006, 8(11), 2377-2380. M. Bssaibis, A. Robert, A. A. Souizi, *J. Chem. Soc. Perkin 1* 1994, 1469-72. M. Murayama, et al., Jpn. Kokai Tokkyo Koho 1973, JP 48075582 19731011

Compounds According to Type 3c

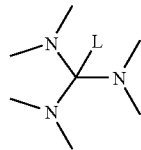

Compounds of this type are for example disclosed in W. Kantlehner, E. Hang et al, *Z. naturforsch. B* 2002, 57(4), 399-419. W. Kantlehner, *Science of Synthesis* 2005, 22, 795-841.

Variant:

Compounds according to the general Typ I with L=H; X, Y=$NR_2$ and Z=OR are for examples disclosed in H. U. Blank, H. Kraus, et al., Eur. Pat. Appl. 1993, EP 525536 A2 19930203. I. Wawer, J. Osek, *J. Chem. Soc. Perkin 2* 1985, 1669-1671.

Modifiability

Dopant Strength:

The effective dopant strength is determined in two ways: a) reduction potential of the imidazolium ion or derivative and b) tendency towards radical formation of the leaving group L, or strength of the C-L bond.

In the test using benzophenone, it was found that L=$CHPh_2$ dopes this material (blue coloring due to formation of the radical anion of benzophenone), whereas no visible reaction takes place with L=$CH_2Ph$, although in suitable matrices a doping effect is achieved (see below). With L=phenyl as a particularly destabilized radical, there is practically no longer any appreciable effect (apart from with respect to strong acceptors as a direct dopant).

With the same structure but different reduction potentials of the imidazolium ions or derivatives, a stronger effect is achieved with 16 (CV: approx. −2.7 V vs. ferrocene) than with 15 (approx. −2.6 V) (see doping experiments).

Volatility:

The tendency towards sublimation of the compounds used according to the invention can easily be adapted in various ways.

While 14 already sublimates in an ultrahigh vacuum at room temperature, in 16 the active part and in 12 the redox-inactive part was modified (use of the heavy benzyl group, which was introduced with little synthetic effort). Both compounds 16 and 12 sublimate in an ultrahigh vacuum at a much higher temperature (at approx. 70° C.) than 14.

Inorganic Leaving Group L

The redox-inactive part L is not limited to organic components: inorganic or organometallic L groups can also be introduced with little effort, as demonstrated with compound 13. This principle is of course not limited to silicon and can be expanded to other fragments.

In principle, therefore, it is also possible for compounds where L=OR and $NR_2$ (W. Kantlehner et al., J. Prakt. Chem. 2000, 342, 256-268) to be used according to the invention.

Processibility

The relatively simple modifiability by varying the leaving group L allows adaptation to various processes and process parameters. In addition to the sublimation temperature, it would also be possible to adjust the solubility in this way.

DESCRIPTION OF THE DOPING EXPERIMENTS

In general, the reduction potentials of n-dopants must meet certain requirements:

Molecule and/or neutral radical with a HOMO level lower than 3.3 eV (preferably lower than 2.8 eV, more preferably lower than 2.6 eV). The HOMO of the donor can be determined from cyclovoltammetric measurements of the oxidation potential. Alternatively, the reduction potential of the donor cation can be determined in a salt of the donor. The donor should have an oxidation potential which versus Fe/Fe+ (ferrocene/ferrocenium redox pair) is less than or equal to approximately −1.5 V, preferably less than or equal to approximately −2.0 V, more preferably less than or equal to approximately −2.2 V.

Molar mass of the donor between 100 and 2000 g/mol, preferably between 200 and 1000 g/mol.

Molar doping concentration between 1:1000 (acceptor molecule:matrix molecule) and 1:2, preferably between 1:100 and 1:5, more preferably between 1:100 and 1:10. In individual cases, a doping ratio may be considered in which the doping molecule is used at a higher concentration than 1:2, for example when a particularly high conductivity is required.

The donor may be formed during the layer production process or the subsequent layer production process from a precursor (see DE 103 07 125.3). The above-specified HOMO level of the donor then relates to the resulting species.

The active part of the materials used according to the invention, i.e. the imidazolium ion or derivative, exhibits in cyclovoltammetric measurements a reduction of between −2.6 V and −2.9 V (versus ferrocene as internal standard).

This means that the dopants used according to the invention (or in actual fact the precursors) exhibit a much greater doping performance than older methods based on a comparable concept.

Doping Experiment 15 in ZnPc 1.5 is co-evaporated with ZnPc in a ratio of 1:10. The sample is illuminated by a mercury vapor lamp for live minutes in the evacuated system through a quartz glass window. After the end of the illumination, the substrate is left to rest for approximately 1 hour and then the conductivity is measured.

A conductivity of $2\times10^{-8}$ S/cm is measured.

Doping Experiment 16 in ZnPc 16 is co-evaporated with ZnPc in a ratio of 1:10. The sample is illuminated by a mercury vapor lamp for five minutes in the evacuated system through a quartz glass window. After the end of the illumination, the substrate is left to rest for approximately 1 hour and then the conductivity is measured.

A conductivity of $7\times10^{-8}$ S/cm is measured.

Doping Experiment 12 in ZnPc 12 is co-evaporated with ZnPc in a ratio of 1:10. The sample is illuminated by a mercury vapor lamp for live minutes in the evacuated system through a quartz glass window. After the end of the illumination, the substrate is left to rest for approximately 1 hour and then the conductivity is measured.

A conductivity of $9\times10^{-8}$ S/cm is measured.

With particular advantage, the dopant strength can be demonstrated in solution with benzophenone. This compound is reduced only at approx. $-2.3$ V (versus ferrocene as internal standard). This value corresponds to the reduction potential of most matrix materials, and this is therefore a useful model compound.

The reduction of benzophenone to form the radical anion (i.e. a successful "doping") is indicated by an intensive blue coloring.

Demonstration of the Doping Strength: Solution of 11 with Benzophenone in THF

In a glovebox flooded with argon, a small sample of 11 is placed along with a ten-fold weight excess of benzophenone and approx. 3 ml of absolute THF in an airtight-scalable NMR tube, spun and held under a commercially available laboratory UV lamp (366 nm) for approx. 10 min. The persistent blue coloring of the solution indicates the successful electron transfer from the n-dopant to the weak acceptor benzophenone. When the tube is opened and the solution is poured out, it is instantly decolored due to contact with air.

Demonstration of the Doping Strength: Solution of 13 with Benzophenone in THF

In a glovebox flooded with argon, a small sample of 13 is placed along with a ten-fold weight excess of benzophenone and approx. 3 ml of absolute THF in an airtight-scalable NMR tube, spun and held under a commercially available laboratory UV lamp (366 nm) for approx. 10 min. The persistent blue coloring of the solution indicates the successful electron transfer from the n-dopant to the weak acceptor benzophenone. When the tube is opened and the solution is poured out, it is instantly decolored due to contact with air.

Demonstration of the Doping Strength: Trituration of 14 with Benzophenone

In a glovebox flooded with argon, a small sample of 14 is finely triturated with a ten-fold weight excess of benzophenone in a small agate mortar and is placed in an airtight-sealable NMR tube, spun and held under a commercially available laboratory UV lamp (366 nm) for approx. 10 min. The persistent blue-green coloring of the solid mixture indicates the successful electron transfer from the n-dopant to the weak acceptor benzophenone. When the tube is opened and emptied, the powder is instantly decolored due to contact with air.

Processing

Production of Doped Layers

The low-molecular layers are typically vapor-deposited using a vacuum method, such, as e.g. VTE (vacuum thermal evaporation) or OVPD (organic vapor phase deposition). Vacuum spray methods may also be used.

Another type of deposition comprises the thermally or optically induced transfer of the material from a carrier substrate to the actual substrate (cf. e.g. LITI: laser induced thermal imaging).

Doped layers are produced in vacuo typically by means of mixed vapor deposition from two independently controlled sources (for matrix material and dopant). Alternatively, they can also be produced by interdiffusion from a dopant layer into the underlying matrix material layer, with the two materials therefore being vapor-deposited one after the other in vacuo. The interdiffusion may be thermally controlled. Under some circumstances, the dopant has to be activated during the production process or in the layer by means of suitable physical and/or chemical measures (e.g. under the effect of light, under the effect of magnetic and/or electric fields).

Alternative production methods for doped layers also include:

mixed vapor deposition of a mixture of matrix and dopant from one and the same source.

doping of a matrix layer by a solution of dopant with subsequent evaporation of the solvent, in particular by means of heat treatment.

surface doping of a matrix material layer by means of a layer of dopant applied to the surface.

production of a solution of matrix molecules and dopant and subsequent production of a layer from this solution by means of conventional methods such as, for example, evaporation of the solvent or spin-coating.

Suitable Matrix Materials

As matrix materials for electron transport layers, use may be made for example of fullerenes, such as for example C60, oxadiazole derivatives, such as for example 2-(4-biphenyl)-5-(4-tert-butylphenyl)-1,3,4-oxadiazole, quinoline-based compounds such as for example bis(phenylquinoxalines), or oligothiophenes, perylene derivatives, such as e.g. perylene-tetracarboxylic acid dianhydride, naphthalene derivatives such as e.g. naphthalenetetracarboxylic acid dianhydride, or other electron transport materials, as described e.g. in A. P. Kulkarni et al., Chem. Mater. 2004, 16, 4556.

As matrix materials for electron transport layers, use may also be made of quinolinato complexes, for example of aluminum or other main group metals, it also being possible for the quinolinato ligand to be substituted. In particular, the matrix material may be tris(8-hydroxy-quinolinato) aluminum. Other aluminum complexes with O and/or N donor atoms may optionally also be used. The quinolinato complexes may contain for example one, two or three quinolinato ligands, the other ligands preferably complexing with O and/or N donor atoms on the central atom, such as for example the following Al complex.

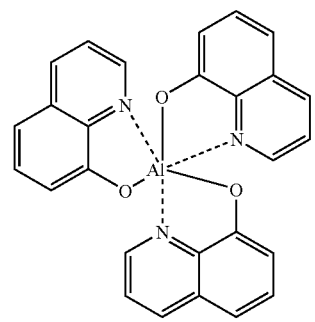

tris[8-hydroxyquinolinato] aluminum(III)

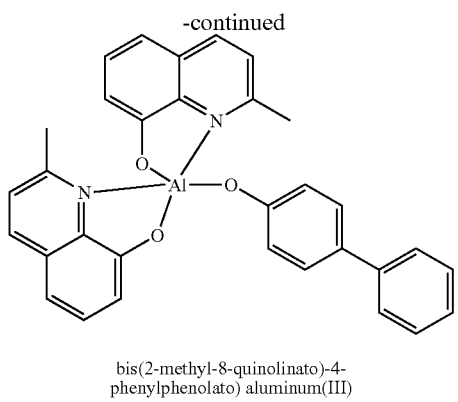

bis(2-methyl-8-quinolinato)-4-phenylphenolato) aluminum(III)

As the matrix material, use may also be made of phenanthrolines which may be substituted or unsubstituted, in particular aryl-substituted, for example phenyl- or naphthyl-substituted, or else for example bathocuproin (BCP). In particular, use may be made of bathophenanthroline (Bphen) as matrix material.

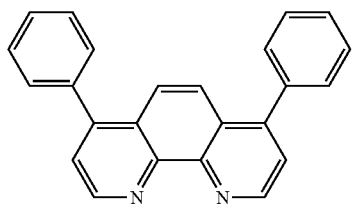

BPhen = bathophenanthroline(4,7-diphenyl-1,10-phenanthroline)

As matrix materials, use may also be made of heteroaromatics such as, in particular, triazole derivatives, optionally also pyrroles, imidazoles, triazoles, pyridines, pyrimidines, pyridazines, quinoxalines, pyrazino-quinoxalines and the like. The heteroaromatics are preferably substituted, in particular aryl-substituted, for example phenyl- or naphthyl-substituted. In particular, use may be made of the following triazole as matrix material.

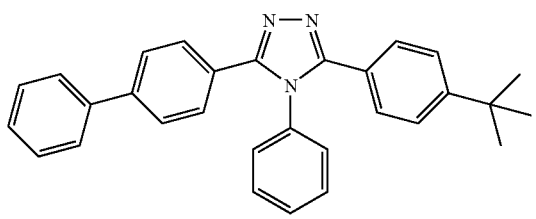

3-(4-biphenylyl)-4-phenyl-5-tert.-butylphenyl-1,2,4-triazole

It will be understood that the aforementioned matrix materials may also be used in a mixture with one another or with other materials in the context of the invention. It will be understood that use may also be method of suitable other organic matrix materials which have semiconductive properties.

Intended Use

Using the described compounds to produce organic semiconductive materials, which may in particular be arranged in the form of layers or electrical conductor tracks, it is possible to produce a large number of electronic components or devices containing these with a doped organic semiconductor layer. In the context of the invention, the term "electronic components" also encompasses optoelectronic components. By means of the described compounds, the electronic properties of an electronically functionally active region of the component can advantageously be modified, such as its electrical conductivity, light-emitting properties or the like. For instance, the conductivity of the doped layers can be improved and/or an improvement in the charge carrier injection from contacts into the doped layer can be achieved.

The invention encompasses in particular organic light-emitting diodes (OLEDs), organic solar cells, organic diodes, particularly those with a high rectification ratio such as 103-107, preferably 104-107 or 105-107, and organic field-effect transistors, which can be produced according to the invention.

In the electronic component, an n-doped layer based on an organic matrix material may be present for example in the following layer structures, the base materials or matrix materials of the individual layers preferably being organic in each case:

M-i-n: metal-insulator-n-doped semiconductor, the layer M forming the metal base contact and possibly being for example ITO, Au, Ag, Al, etc. The cover contact forms an ohmic contact with the n-doped layer and may consist for example of Al. The layer "i" is an undoped layer.

n-i-M: the same as stated in respect of the M-i-n structure applies, but with the difference that the ohmic contact is provided on the substrate.

p-i-n: p-doped semiconductor-insulator-n-doped semiconductor.

n-i-p: n-doped semiconductor-insulator-p-doped semiconductor.

"i" is once again an undoped layer, "p" is a p-doped layer. The contact materials here are hole-injecting, it being possible for example for a layer or a contact comprising ITO or gold to be provided on the p-side, or are electron-injecting, it being possible for example for a layer or a contact comprising ITO, aluminum or silver to be provided on the n-side. In the above structures, the i layer may also be omitted if necessary, as a result of which layer sequences with p-n or n-p transitions may be obtained.

However, the use of the described compounds is not limited to the examples of embodiments mentioned above. In particular, the layer structures may be supplemented or modified by introducing additional suitable layers.

The compounds according to the invention and the derivatives thereof can be used according to the invention in the electronic components but also in layers, conductor tracks, spot contacts or the like when these are predominant over another component, for example as an injection layer in pure or essentially pure form.

In another configuration, the n-dopant according to the invention may also be used to improve the injection from the cathode. To this end, it is provided to form a layer, essentially consisting of the dopant, between the cathode and an electron-transporting layer. A layer essentially consisting of the dopant may have a layer thickness of more than 0.5 nm, preferably between 0.5 nm and 20 nm, more preferably between 1 nm and 10 nm, even more preferably between 1 nm and 3 nm. A layer essentially consisting of the dopant may be formed as a pure layer of the dopant.

In the case of processing from solution, finished formulations of matrix (optionally also a semiconductive polymer) and dopant in solution may be provided.

A formulation of monomer and dopant is also conceivable, the released radicals starting a polymerization of the monomers after activation of the dopant.

Furthermore, it is easily possible to combine other functionalities, e.g. coupling of the dopant to host materials.

The features of the invention which are disclosed in the above description and in the claims may be essential both individually and in any combination for implementing the invention in its various embodiments.

The invention claimed is:

1. An electronic or optoelectronic component comprising a precursor of a n-dopant, wherein the precursor of a n-dopant is a dopant for doping an organic semiconductive material, a blocking layer, a charge injection layer, an electrode material, a storage material or a semiconductor material itself in the electronic or optoelectronic component, wherein the precursor is selected from the group consisting of formulae 3, 3a, and 3b:

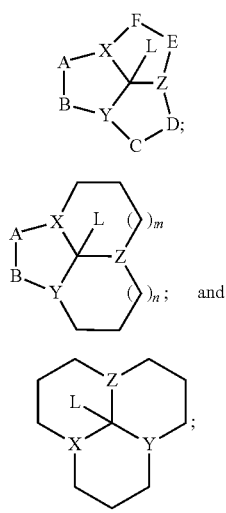

wherein

L is an organic, inorganic, or organometallic leaving group selected from the group consisting of H, sec-aliphatic-alkyl, tert-aliphatic-alkyl, $CH_2Ar$, $CHAr_2$, $SiAr_3$, $SiAr_2$-alkyl, and $SiAr$-alkyl$_2$;

wherein Ar is aryl;

A-B, C-D, and E-F independently of one another are placeholders for one or more $sp^3$- or $sp^2$-hybridized carbon atoms;

in formulae 3, 3a, and 3b, X, Y and z independently are N or P;

n is an integer from 0 to 2; and m is an integer from 0 to 2.

2. The component according to claim 1, wherein A-B, C-D, and E-F independently of one another are placeholders for —$(CH2)_o$— wherein o is 1-3, —CH=CH—, or independently of one another are part of a fused unsubstituted or substituted aromatic.

3. The component according to claim 2, wherein A-B, C-D, and E-F independently of one another are part of a 1,2-benzo, 1,8-naphtho, 2,3-naphtho, 2,3-thieno, 2,3-furano, 2,3-pyrrolo, 2,3-(1,4-dioxano), or 2,3-(1,4-diazino) skeleton.

4. The component according to claim 2, wherein the fused aromatic comprises one or more substituents selected from the group consisting of alkyl, alkoxy, dialkylamino, and diarylamino.

5. The component according to claim 1, wherein the precursor is selected from the group consisting of the following formulae:

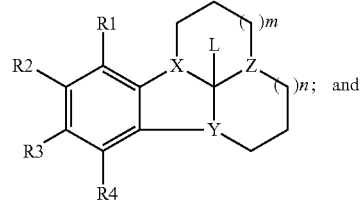

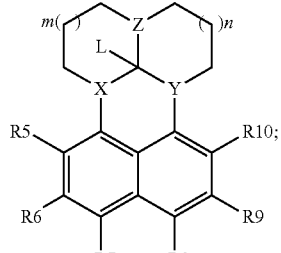

wherein

L is an organic, inorganic, or organometallic leaving group selected from the group consisting of H, sec-aliphatic-alkyl, tert-aliphatic-alkyl, $CH_2Ar$, $CHAr_2$, $SiAr_3$, $SiAr_2$-alkyl, and $SiAr$-alkyl$_2$; wherein Ar is aryl;

in formulae 3d and 3e, X, Y and z independently are N or P;

n is an integer from 0 to 2;

m is an integer from 0 to 2; and wherein R1-R10 independently of one another are selected from the group consisting of H, $C_1$-$C_{10}$ alkyl, $C_6$-$C_{12}$ aryl, $C_1$-$C_{10}$-alkoxy, and $C_1$-$C_{10}$-dialkylamine.

6. The component according to claim 1, wherein the precursor is converted into a n-dopant by activation with electromagnetic radiation.

7. The component according to claim 6, wherein the electromagnetic radiation is visible light, UV light, or IR light.

8. A compound according to one of formulae 3d or 3e:

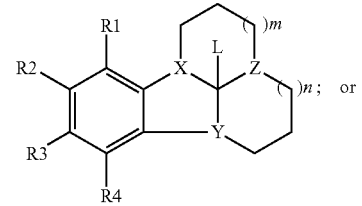

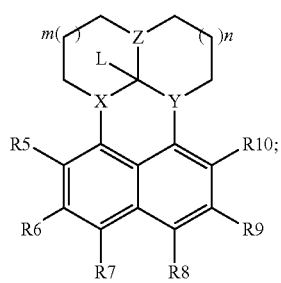

wherein
L is an organic, inorganic, or organometallic leaving group selected from the group consisting of H, sec-aliphatic-alkyl, tert-aliphatic-alkyl, $CH_2Ar$, $CHAr_2$, $SiAr_3$, $SiAr_2$-alkyl, and $SiAr$-$alkyl_2$; wherein Ar is aryl;
in formulae 3d and 3e, X, Y and z independently are N or P;
n is an integer from 0 to 2;
m is an integer from 0 to 2;
wherein R1-R10 independently of one another are selected from the group consisting of H, $C_1$-$C_{10}$ alkyl, $C_6$-$C_{12}$ aryl, $C_1$-$C_{10}$-alkoxy, and $C_1$-$C_{10}$-dialkylamine; and
excluding compound 3e wherein L=H and R1-R10=H.

9. The component according to claim 1 comprising an organic semiconductive material comprising at least one organic matrix compound and one dopant, wherein the precursor of a n-dopant is the dopant.

10. The component according to claim 9, wherein the molar doping ratio of dopant to matrix molecule or the doping ratio of dopant to monomeric units of a polymeric matrix molecule is between 20:1 and 1:100 000.

11. The component according to claim 1, wherein the component comprises an electronically functionally active region, wherein the electronically active region comprises the precursor of a n-dopant.

12. The component according to claim 11, wherein the electronically functionally active region comprises an organic semiconductive matrix material which is doped with at least one dopant in order to modify the electronic properties of the semiconductive matrix material, wherein the dopant is the precursor of a n-dopant.

13. The component according to claim 11, wherein the component is an organic light-emitting diode, a photovoltaic cell, an organic solar cell, an organic diode, an organic field-effect transistor or a photo-initiated or magnetic storage means.

* * * * *